United States Patent [19]

Link et al.

[11] Patent Number: 4,908,036
[45] Date of Patent: Mar. 13, 1990

[54] ENDOPROSTHESIS

[75] Inventors: Helmut D. Link, Hamburg; Arnold Keller, Kayhude, both of Fed. Rep. of Germany

[73] Assignee: Waldemar Link GmbH & Co., Hamburg, Fed. Rep. of Germany

[21] Appl. No.: 200,758

[22] Filed: May 31, 1988

[30] Foreign Application Priority Data

Jun. 15, 1987 [DE] Fed. Rep. of Germany ... 8708419[U]

[51] Int. Cl.⁴ .......................... A61F 2/36; A61F 2/28; A61F 2/30; A61F 2/32
[52] U.S. Cl. ....................................... 623/23; 623/16; 623/18; 623/22
[58] Field of Search ................................... 623/23, 18

[56] References Cited

U.S. PATENT DOCUMENTS

| 4,012,796 | 3/1977 | Weisman et al. | 623/18 |
| 4,698,063 | 10/1987 | Link et al. | 623/3 |
| 4,705,032 | 11/1987 | Keller | 623/23 |
| 4,783,192 | 11/1988 | Wroblewski et al. | 623/23 |

FOREIGN PATENT DOCUMENTS

| 0041591 | 12/1981 | European Pat. Off. | 623/3 |
| 2724234 | 12/1977 | Fed. Rep. of Germany | 623/23 |
| 3125657 | 1/1983 | Fed. Rep. of Germany | 623/23 |

Primary Examiner—Richard J. Apley
Assistant Examiner—Stephanie L. Iantorno
Attorney, Agent, or Firm—Chilton, Alix & Van Kirk

[57] ABSTRACT

Endoprosthesis having a stem to be anchored in the bone and a separate bone support. The devices for holding the bone support on the shaft are designed such that the bone support is pivotable, preferably spherically mobile, so that it adjusts itself automatically to the position of the bore surface supporting it.

9 Claims, 1 Drawing Sheet

Fig. 1
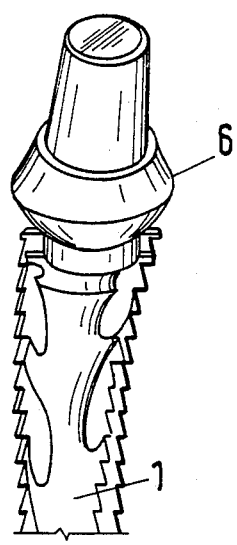
Fig. 2
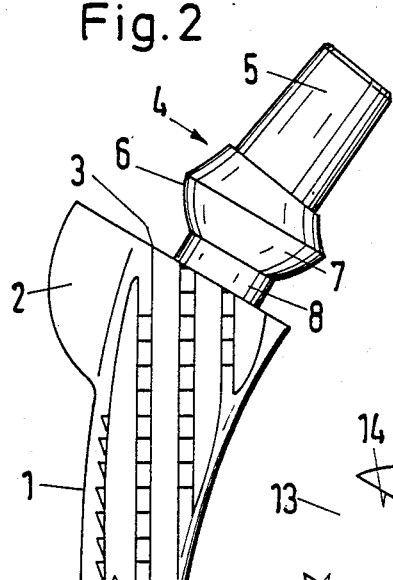
Fig. 3
Fig. 4
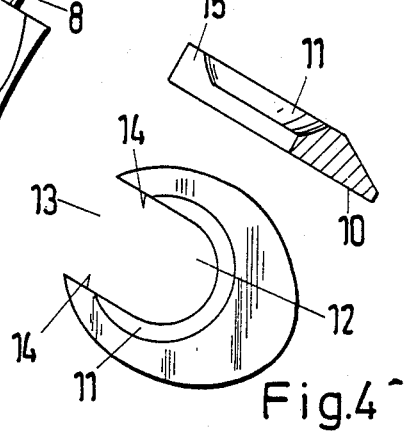
Fig. 5
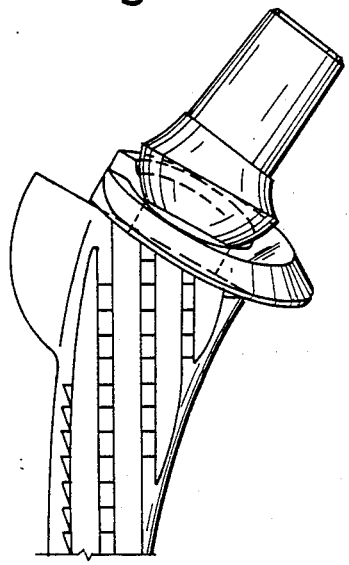
Fig. 6
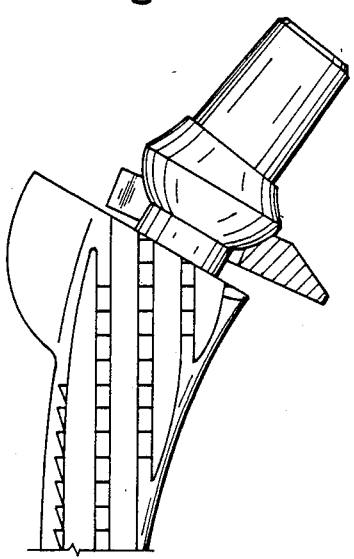

ENDOPROSTHESIS

DESCRIPTION

The invention relates to an endoprosthesis for replacement of a bone part, in particular to hip joint prosthesis, comprising a stem which is to be anchored in a bone cavity and a separate bone support which extends transversely to the stem and is held by interacting holding devices arranged on the bone support and on the upper stem end.

Accurate contact of the bone support of the prosthesis with the corresponding bone surface is a desirable feature, especially in the case of cement-less implantation. This applies especially to the bone support of a hip joint endoprosthesis which transmits a substantial part of the body load to the resection surface of the femur bone. Because the resection cut severing the neck is frequently not sufficiently accurate for full-area contact of the bone support, a special instrument is available to the surgeon for a further, plane-parallel resection of the femur bone. This includes a femoral neck cutter which is passed over a guage, inserted into the rasped-out medullary canal of the femur bone, in such a way that all the angles of the resection surfaces are the same as the angles of the bone support and positive seating of the bone support on the bone is achieved. This further resection prolongs the duration of the operation and is therefore undesirable in many cases, especially for elderly patients.

To avoid further resection, it is known (EP-A 0,158,014; DE-A 2,305,333) to use a large number of alternatively useable bone support plates which, on the one hand, can be joined at fixed angle to the prosthesis stem, but, on the other hand, have a lower surface inclined at various angles for adaptation to different angular positions of the resection surface. Their use presupposes that the angular position of the resection surface is accurately measured relatively to the direction of the prosthesis, and this is often difficult under operation conditions and can lead to a faulty selection. Moreover, for cost reasons, the exchangeable bone supports can be made available only in relatively wide angle gradations, so that certain deviations in the angle between the bone support surface of the prosthesis and the resection surface are not excluded.

It is the object of the invention to achieve a snug fit of the prosthesis and nevertheless to avoid the necessity of a further resection.

According to the invention, this is achieved when the holding devices securing the bone support on the upper stem end are designed to be pivotable, so that the bone support is automatically aligned with the respective bone surface.

In some cases, pivotability about one axis may be sufficient; in general, however, mobility in all directions is preferred. For this purpose, holding devices are suitable which are formed by an annular projection with a convex-spherical lower surface on the stem side and by a corresponding counter-surface on the side of the bone support, this counter-surface advantageously being a spherical recess.

The bone support advantageously has the shape of a horse-shoe and can be slipped over the stem from the side, as is known per se (EP-PS 0,093,230; DE-U 8,212,788).

The invention is explained in more detail below with reference to the drawing which illustrates an advantageous examplary embodiment of a hip joint prosthesis in which;

FIGS. 1 and 2 show two side views of the upper part,
FIGS. 3 and 4 show a longitudinal section and a plan view of the bone support, and
FIGS. 5 and 6 show side views of the stem joined to the bone support.

The stem part 1 which is to be anchored in the femur bone and which can be shaped in any desired, conventional manner, its lower part not being shown in the drawing, carries a trochanter spur 2 and ends in the upper end face 3, from which the neck part 4 projects. The upper section 5 of the neck part is of conical shape for receiving the articular head. It also carries an annular projection 6, the lower surface 7 of which is of spherically convex shape. Between this surface 7 and the upper end face 3 of the stem part 1, the neck forms a groove-like constriction 8.

The bone support 9 has a plane lower surface 10 which is intended to be supported on the resection surface of the femur bone. The upper side contains a concave spherical recess 11, which essentially has the same radius of curvature as the spherical lower surface 7 of the annular projection 6. The bone support 9 has the shape of a horse-shoe, with a cut-out, the inner part 12 of which has a circular boundary, concentrically to the recess 11, whereas its outer part 13, the width of which is equal to that of the inner part 12, opens outwards between parallel boundaries 14. Looking at the boundary surfaces 14, it will be seen that their height is reduced in the inner region by the spherical annular recess 11, whereas it is increased in the region 15 near to the outer periphery of the bone support.

The dimensions are selected such that the bone support 9 can, in the region of the constriction 8, be slipped over the neck of the prosthesis stem, as indicated in FIG. 5. When the prosthesis is implanted, the lower surface 10 comes to lie on the resection surface of the femur bone, the spherical surface 7 of the annular projection 6 coming to lie on and being supported in the correspondingly spherical recess 11 of the bone support, as shown in FIG. 6. Due to the spherical shape of these parts, the bone support is freely adjustable with regard to the angle and can therefore make full-area contact with the resection surface even if the latter should not be absolutely at right angles to the corresponding part of the prosthesis stem. Full-area support and most favourable force transmission are ensured even if a shift of the prosthesis in the bone or a change in the bone shape should occur in the course of time.

The pivotable or spherically mobile holders, 7, 11 acting between the bone support and the stem, can be of any desired shape. In the preferred embodiment shown in the drawing, the centre 16 of curvature of the spherical surface 7 lies near to the centre axis 17 of the neck part 4. It can also be advantageous if the centre is in a position medially away from the axis 17, especially near to the line 18. In the case of a patient standing upright, this is the perpendicular through the force-transmitting contact surface between the lower surface 10 of the bone support and the bone. A position of the centre 16 between the lines 17 and 18 can also be very advantageous.

The important point is that, when the prosthesis stem is driven in, the bone support automatically comes to lie positively on the resection surface, which may possibly be in an oblique position, of the femur bone. In the embodiment shown, sufficient space must be present between the lower surface 10 of the bone support and the upper end face 3 of the stem part 1, so that the bone support can also align itself obliquely if this is required by the position of the resection plane.

The removeability of the bone support is not a prerequisite for the pivotability of the bone support. Rather, the bone support can be irreleaseable, albeit mobile, on the prosthesis shaft at the factory.

Even though the advantages of the invention are particularly obvious in the case of hip joint prostheses, it is also applicable to other prostheses, in which a part of the force is transmitted from the prosthesis via a bone support to a resected or naturally present surface of the respective bone, for example shoulder prostheses, elbow joint prostheses, knee joint prostheses and finger joint prostheses. The bone support which is a part which is separate from the stem can be rigidly joined to other prostheses parts, for example to a part forming a joint.

We claim:

1. Endoprosthesis for insertion into a bone cavity as a replacement of a bone part, comprising:
    a stem having anterior, posterior, medial and laceral sides, said stem including a lower portion which is to be anchored in the bone cavity and an upper portion which is to project out of the cavity;
    first holding means formed in the stem upper portion; and
    a separate bone support collar which extends transversely to the stem having a distal surface for engaging a resected surface of the bone and a proximal surface having second holding means formed therein for pivotally mounting the bone support collar to the first holding means of said stem upper portion, for the duration of the implantation.

2. Endoprosthesis according to claim 1, characterized in that the holding means are pivotable in all directions.

3. Endoprosthesis according to claim 2, characterized in that the first holding means are formed by an annular projection (6) with a convex-spherical lower surface (7) on the stem and the second holding means are formed by a corresponding recess (11) on the proximal surface of the bone support collar.

4. Endoprosthesis according to claim 1, characterized in that the bone support collar (9) has the shape of a horseshoe and can be slipped over the stem from any one of the sides.

5. Endoprosthesis according to claim 2, characterized in that the bone support collar (9) has the shape of a horseshoe and can be slipped over the stem from any one of the sides.

6. Endoprosthesis according to claim 3, characterized in that the bone support collar (9) has the shape of a horseshoe and can be slipped over the stem from any one of the sides.

7. The endoprosthesis of claim 1, wherein the support collar has an opening through which the stem upper portion passes, the stem upper portion has a longitudinal axis passing through the support collar opening, and the support collar can assume a range of angular orientations for the duration of the implantation with respect to the stem axis passing therethrough.

8. The endoprosthesis of claim 3, wherein the support collar has a substantially flat distal surface for substantially planar, force transmitting contact with a substantially flat bone resection surface defining the entrance to said bone cavity.

9. The endoprosthesis of claim 8, wherein the lower surface of the annular projection on the stem is mounted in a corresponding spherical segment surface defining said recess on the proximal side of the bone support collar, and wherein the distal surface of the support collar is free of contact with any portion of the stem.

* * * * *

UNITED STATES PATENT AND TRADEMARK OFFICE
CERTIFICATE OF CORRECTION

PATENT NO. : 4,908,036
DATED : March 13, 1990
INVENTOR(S) : Helmut D. Link et al It is certified that error appears in the above-identified patent and that said Letters Patent is hereby corrected as shown below:

Column 3, line 3 of claim 1, "laceral" should be --lateral--.

Signed and Sealed this

Fourteenth Day of July, 1992

Attest:

DOUGLAS B. COMER

*Attesting Officer*     *Acting Commissioner of Patents and Trademarks*